United States Patent [19]
Knopf et al.

[11] Patent Number: 4,799,358
[45] Date of Patent: Jan. 24, 1989

[54] APPARATUS FOR COOLING AND DEEP FREEZING SAMPLES OF BIOLOGICAL MATERIAL ENCLOSED IN VESSELS

[75] Inventors: Ulrich C. Knopf, Freiburg; Joseph Sieber, Zurich, both of Switzerland

[73] Assignee: Agrogen Stiftung, Freiburg, Switzerland

[21] Appl. No.: 143,646

[22] Filed: Jan. 13, 1988

[30] Foreign Application Priority Data

Jan. 19, 1987 [CH] Switzerland .................. 00164/87

[51] Int. Cl.$^4$ ............................................. F25B 21/02
[52] U.S. Cl. .......................................................... 62/3
[58] Field of Search ...................................... 62/3, 457

[56] References Cited

U.S. PATENT DOCUMENTS

| | | | |
|---|---|---|---|
| 2,922,284 | 1/1960 | Danielson et al. | 62/3 |
| 2,959,925 | 11/1960 | Frantti et al. | 62/3 |
| 3,194,023 | 7/1965 | Sudmeier | 62/3 |
| 3,402,561 | 9/1968 | Mahoney | 62/3 |
| 4,364,234 | 12/1982 | Reed | 62/3 |
| 4,453,385 | 6/1984 | May | 62/3 |

*Primary Examiner*—Lloyd L. King
*Attorney, Agent, or Firm*—Frank P. Presta

[57] ABSTRACT

Apparatus for cooling and deep freezing samples of biological material. The cooling zone, containing the closed plastic vessels with the samples, is enclosed between two parallel, plate-like layered cooling elements. The latter are made of at least two cooling layers containing blocks of Peltier elements, alternating with plates of a heat-conducting metal, preferably aluminium. The disposition with several layers of Peltier elements increases the temperature difference between the inner space and environment. The innermost layer of the cooling elements is a metal plate as well; the outermost layer is a metal plate with means for external cooling, such as channels for circulating water or cooling ribs. The cooling zone is either a metal block with cavities to receive the sample vessels or simply the free space between the two innermost plates of the cooling elements, into which the vessels can be inserted. In one special design the metal block is an exchangeable module or cassette to be inserted into the cooling space. All parts, except the plates cooled externally, are thermally insulated; the cooling space is sealed against humidity by an insulated lid. The apparatus is controlled by a programmable electronic unit, by which a temperature program for the freezing process can be followed. The signals are given by temperature sensors in the cooling zone. In a preferred design, the freezing apparatus, the electronic control unit and the power supply are combined together in portable housing box.

20 Claims, 9 Drawing Sheets

APPARATUS FOR COOLING AND DEEP FREEZING SAMPLES OF BIOLOGICAL MATERIAL ENCLOSED IN VESSELS

BACKGROUND OF THE INVENTION

The preferred method today for conserving biological material while simultaneously maintaining its viability is deep freezing, followed by storage at temperatures below $-30°$ C. Cells such as spermatozoa, fertilized or unfertilized eggs, animal and plant cells cultivated in vitro, tissue samples, blood and other biological material can thus be stored over practically unlimited times and, if desired, brought back to life by thawing. The method is important in biological research, in animal and plant breeding and in the implanting of fertilized eggs or embryos, as practised recently in human medicine and animal husbandry.

When freezing living biological material, it is very important to lower the temperature regularly and at a rate at which any damage to the cells and their components is avoided. Damage can happen at too high (supraoptimal) or too low (suboptimal) rates of temperature reduction. Damage at supraoptimal cooling rates is very probably produced by development of ice crystals inside the cell and by the expansion of the crystals during the reheating phase (see P. Mazur: The role of intracellular freezing in the death of cells cooled at supraoptimal rates, *Cryobiology* 14, 251-272, 1977). Damage at suboptimal cooling rates can be explained by so-called solution effects (see P. Mazur: Slow freezing injury in mammalian cells, in "The Freezing of Mammalian Embryos", CIBA Foundation Symposium 52, 19-48, 1979). Safe methods for freezing biological samples therefore need a temperature program, exactly to be controlled, which depends on the type of material and the size of the sample.

The type of vessel in which the material is enclosed depends on the size of the sample as well. For greater quantities of material ampullae, preferably made of plastics, can be used, whose capacity is between about 2 and 10 milliliters, or tubes with a capacity of 0.25 to 0.5 milliliters; for single cells, sperm cells and embryos, thin plastic tubes, so-called "straws" with a diameter of 1.95 millimeters and a length of about 14 centimeters are preferred. Together with their surrounding liquid the specimen can be sucked into the straw, which, after this, is closed on both its ends. Because of their small volume, these straws allow an exact temperature control with minimal time lag.

Devices for deep freezing of biological samples of different description are commercially available. In one type of the known devices the sample vessels are kept in a bath made with a non-freezing liquid, such as freon, alcohol, methanol or isopentane, whereby the temperature of this bath is kept uniform by stirring or by circulation. In another type of apparatus the sample vessels are kept in a space with a circulating gas, which is held at a temperature as even as possible. The volume of liquid or gas is cooled by heat exchange with a cryogen, such as liquid nitrogen, or by a conventional freezing machine. A controlled heat source is used to keep the gaseous or liquid bath at the desired exact temperature. For this latter operation additional energy has to be spent, as well as for the amount of cryogen lost by evaporation.

By its nature this type of apparatus is relatively heavy and needs a lot of energy. A high expenditure of weight, volume and energy has to be made, only to cool and freeze a relatively small sample. Smaller apparatus with a better use of weight, volume and energy is therefore highly desirable.

SUMMARY OF THE INVENTION

This invention concerns a new apparatus for cooling and deep freezing of samples of biological material, by which the drawbacks of the known devices as described above can be avoided. According to the invention the samples are arranged inside a cooling zone which is enclosed between two platelike cooling elements. The cooling elements consist of a layered arrangement of at least two layers of Peltier elements superposed onto one another alternatingly with plates of a thermoconducting metal in such a manner that the metal plates form interlayers between the layers of Peltier elements and enclose the whole structure on both sides.

The use of Peltier elements to generate cold for cooling goods such as biological material has already been described in the German Offenlegungsschriften Nos. 16 01 036 and 32 38 325 as well as in the U.S. Pat. Nos. 2,922,284 and 2,959,925. Certain disadvantages of the devices hitherto used can be avoided by these inventions. Peltier elements are able to convert an electrical current directly into useable heat or cold. They are relatively small and can directly brought into contact with the samples to be frozen, without the need for a liquid or gaseous temperature bath. However a serious drawback of Peltier elements is their low performance; in particular it is difficult to reach a high temperature difference between the active poles of an element. Temperatures of $-30°$ C. and lower as needed in deep freezing biological samples are therefore only obtained with great difficulty. In particular, the time needed to reach such low temperatures is long and very probably does not correspond to the optimal cooling speed.

Peltier elements represent an inversion of the so-called Seebeck effect, which is well known from e.g., thermoelements. Preferably they are made of two semiconductors, one each of the n- and p-types respectively. The ends of these semiconductors are soldered together, in order to form a closed conducting loop. If a direct current is sent through this loop, one of the links between the semiconductors is heated while the other link is cooled. Which of the two links is cooled or heated depends on the direction of the current: At the hot pole the current flows from the p- to the n-semiconductor, and vice-versa. Semiconductors which are well suited for building Peltier elements are e.g., alloys of Silicium and Germanium, doped with Arsen (n-type) or Bor (p-type).

The use of the Peltier element as a cooling device depends on the withdrawal of heat which is generated at the hot pole. The cold pole then takes a temperature below that of its surroundings. The performance of a Peltier element depends on two parameters: Heat conduction between the two poles, which tends to reduce the temperature difference between them, and ohmic resistance, which generates undesired heat inside the element. The temperature difference, which can reached between the poles is therefore limited by these two effects and cannot be increased arbitrarily, i.e., by increasing the intensity of the electric current. Furthermore the energy output of one single Peltier element, consisting of two single semiconductors with their soldering points is very low. It can be multiplied by building blocks, in which a great number of single Peltier elements are united, with the elements linked electrically in series and thermally in parallel, so that one surface of the block represents the hot pole and the opposite surface the cold pole of the block. Such blocks of Peltier elements are commercially available in the form of rectangular plates whose two greatest surfaces constitute the two thermal poles.

The thermal output of the Peltier elements can thus be amplified as desired, but the temperature difference between the poles remains limited by the reasons cited above. To increase this difference, a number of Peltier blocks has to be piled onto one another to build a cascade with the thermal poles all in the same direction. In this manner, the temperature differences between the poles of the single blocks add together. In other words, by using a number of Peltier layers in a superposed cascade-like arrangement, the temperature difference between the cooling zone and the environment can be divided into several steps; thus the temperature difference over one single cooling layer is reduced and within reach of a Peltier element.

Therefore, according to the invention, the cooling elements of the deep freezing apparatus are layered, with at least two superposed layers of Peltier blocks, alternating with plates of a heat-conducting metal, preferably aluminium, between them and completed on both sides by a metal plate as well. The cold poles of all Peltier elements are oriented toward the cooling zone and the hot poles toward the outside of the apparatus. From the outermost metal plate heat is withdrawn by external cooling means, such as channels for cooling water inside this plate or cooling ribs on its outer surface. Two such layered cooling elements, each consisting of alternating layers of Peltier blocks and heat conducting metal plates confine the cooling zone of the apparatus between them. By this arrangement, it is easily possible to reach the low temperatures of $-30°$ C. and still less inside the cooling zone, in a time lapse which is compatible with the cooling speed necessary for optimal deep freezing of biological specimen.

The cooling zone can be adapted to the specific task to be performed. To freeze samples which are enclosed in ampullae or tubes it is advantageous to use a metal block, preferably of aluminium, having cavities to receive the vessels containing the biological specimen. A close fit between the vessels and the walls of the cavity is preferred for good heat transition. Instead of cavities inside the block, grooves at its outer surface or on the surface of the innermost cooling plate can be used as well. This design is especially suited for vessels in the form of thin straws (FIG. 3).

In a special design the cooling block has the form of a module or cassette, which can be inserted or withdrawn from the apparatus by simple manipulation. It is therefore possible to exchange blocks after completion of a freezing cycle, or to use metal blocks of the same outer dimensions which are disposed to receive different kinds of vessels (FIG. 5).

Still another possibility is the use of metal blocks consisting of two parts which can be separated or hinged apart. This creates the possibility to enclose the vessels for the biological specimen completely inside the cooling block (FIG. 4).

Instead of using a metal block, the vessels containing the biological samples can directly be inserted into the space between the innermost plates of the two cooling elements. In order to have a good cooling effect and a temperature as uniform as possible, the vessels should be in direct contact with the plates of the two cooling elements. In this design it is advantageous to make the innermost plates of the cooling elements of one single piece of metal with an interconnection at the bottom in the form of a bridge between the plates, as shown in FIG. 1. Thus the cooling block of this design is directly formed by the two innermost plates of the cooling elements and cannot be withdrawn from the apparatus.

In another design, which is especially suited for working with straws, there is no cooling block; the cooling zone is represented by the free space between the innermost plates of the cooling elements. In this case the space has the form of a small slot, whose width corresponds exactly to the diameter of the straws (FIG. 2)

With all designs of the apparatus it is necessary to insulate all cold surfaces in order to prevent heat losses and to close all the inner spaces against the access of moist air in order to prevent the forming of ice on the cold surfaces outside or within. The two outer plates of the cooling elements, which are cooled externally, normally need no insulation. At the site, where free access to the cooling zone is needed, the insulation must be in the form of a removable lid.

In the design where the cooling zone consists of a narrow slot for receiving the straws, a simple and advantageous form of the closure consists of a flexible rubber plate, into which a slit has been cut, extending over the whole length of the cooling slot. Together both sides of this slit form two lips, which are tightly closed. Due to their small diameter straws can be inserted into and withdrawn from the cooling slot through the two flexible lips without substantially impairing the tightness of the seal. (FIG. 2)

In another design of the apparatus, the depth of the cooling zone is greater than the length of a straw, and the straw is entirely within the cooling zone. In order to introduce or withdraw the straws, a stopper made of an insulating plastic material is fitted into the straws, this stopper being of sufficient length to protrude out of the closing slit of the cooling zone (FIG. 2).

In a further special design this stopper is made partly of metal, and partly of an insulating plastic material, whereby the metallic portion fits into the straw and extends beyond the upper end of the straw. This latter part of the stopper has exactly the same diameter as the straw, fitting closely between the plates of the cooling elements. Heat transition between the cooling plates and the biological sample is thus improved (FIG. 8a,). Heat transition can still further be improved by lenghtening the metallic part inside the straw in a needlelike form, with the point of the needle penetrating into the liquid part of the sample (FIG. 8b, 8c). Nucleation of the biological sample by a momentary temperature shock can be facilitated by this design.

As mentioned before, in the procedure of deep freezing biological samples an exact temperature program has to be followed in order to avoid damage to the samples. The output of the cooling elements has therefore to be controlled as a function of the temperature as measured in the cooling zone and of the programme to be followed. This can be done by a programmable microcomputer, together with one or several temperature sensors in the cooling zone and/or inside the cooling elements. Thermoelements, thermistors or resistance sensors can be used for this purpose. In the control programme at least one slope function has to be provided for, in order to bring about a uniform change of temperature during a preset interval of temperature or time. Very advantageously, not only lowering, but raising as well, of the temperature should be programmable in order to use the apparatus for the thawing of samples. An indicating and/or recording thermometer should be comprised in the control circuit. Very advantageously the energy input into the Peltier elements can be controlled by feeding them with a pulsed direct current, the pulse-to-pause ratio determining the total energy input in a given interval of time. The a.c. input from the mains may be chopped in order to have a compact alimentation unit.

In a preferred form of the invention the cooling unit, the control circuit and the electric alimentation are united in a portable housing box.

To satisfy other needs of a biological laboratory, the apparatus according to the invention can be used of course to cool specimen to temperatures above the freezing point and for keeping them at these temperatures.

The disposition of the apparatus will be illustrated and explained in more detail by the drawings FIGS. 1 to 9, without restricting by them the scope of the invention.

DESCRIPTION OF THE PREFERRED EMBODIMENT

Figure 1:
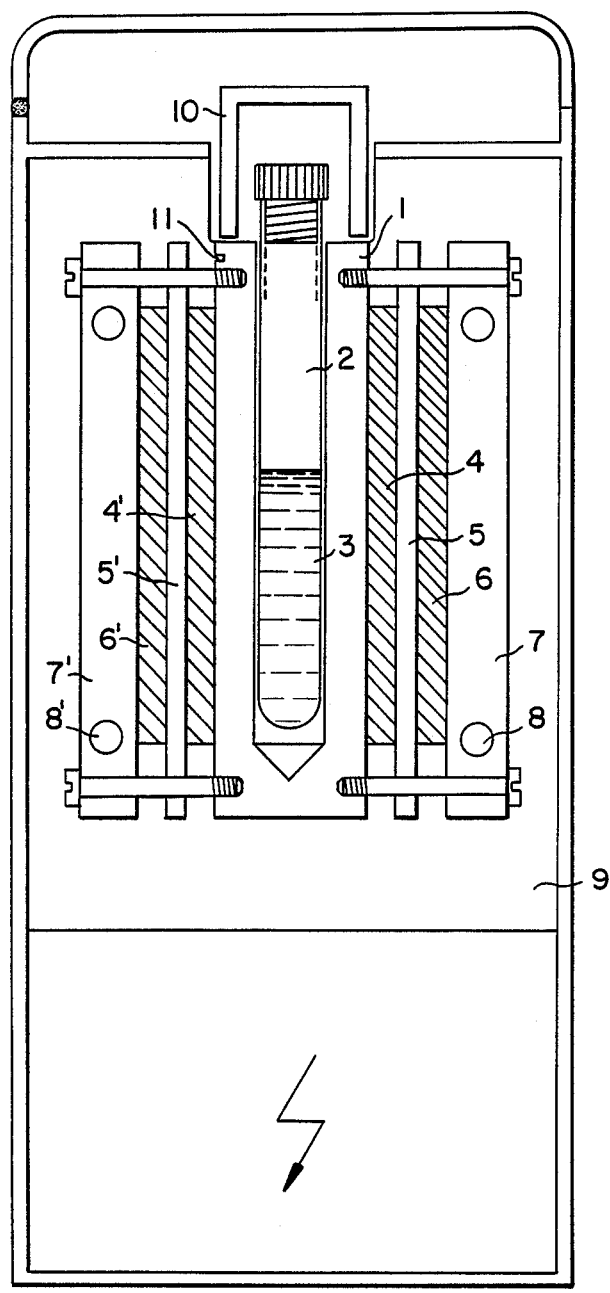

FIG. 1 shows one possible design of the apparatus according to the invention, in a schematic elevation. In a cavity of the cooling block (1) a vessel in the form of an ampulla (2) containing the biological material (3) is inserted. The two cooling elements on both sides of the cooling block consist of the blocks of Peltier elements (4,4' and 6,6') and the aluminium plates (5,5' and 7,7'). Cooling channels (8,8') are provided in the outer plates (7,7'), through which a liquid or gaseous cooling medium can be circulated. In another design which is not shown, the plates (7 and 7') are provided with cooling ribs, onto which, if necessary, air can be blown. In the design shown in the figure the cooling block (1) is formed by the innermost plates of the two cooling elements, which, in this case, are made of one single piece of metal and are connected at their lower end by a bridge (claim 5). At their sides and at the lower end, the cooling block and the parts (4,4', 5,5' and 6,6') are surrounded by a thermal insulating layer (9), whereas the space above remains free and will be covered by an insulating lid (10). At the point (11) of the cooling block a temperature sensor is provided.

Figure 2:
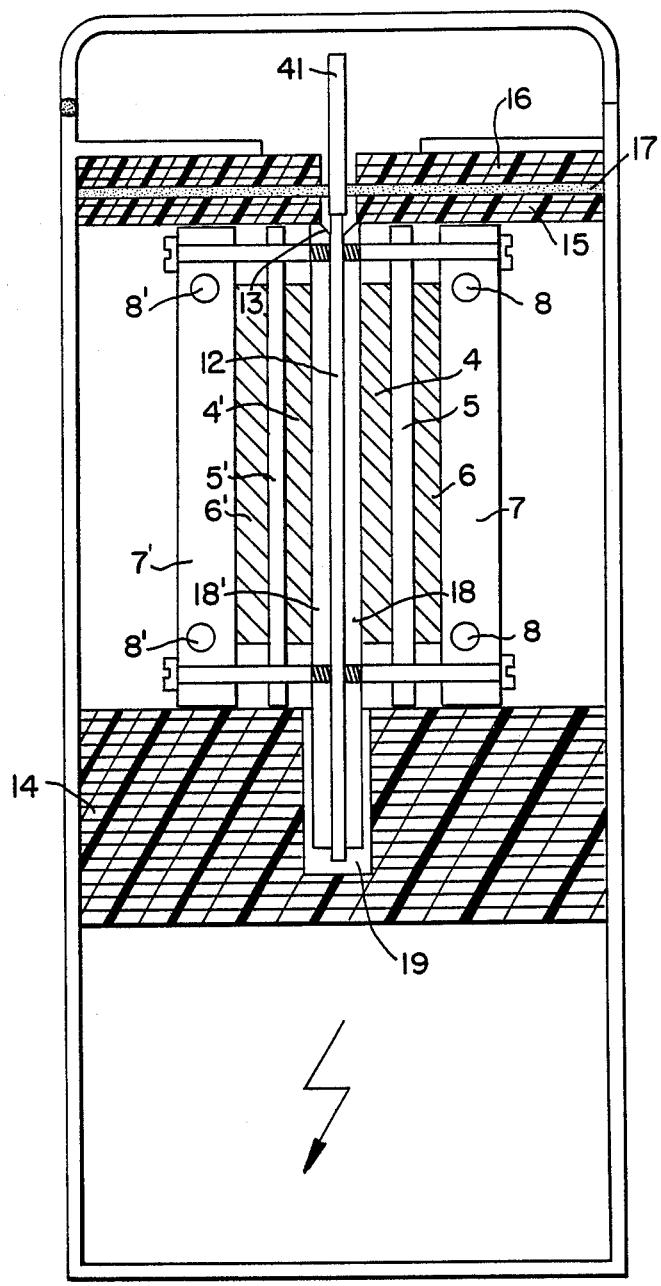

In FIG. 2 another form of the apparatus according to FIG. 1 is shown in elevation. The space between the two innermost plates of the cooling elements is narrow. Straws (12), in which the biological specimen are enclosed, are directly inserted into the slot between the plates (18,18') of the cooling elements. The upper edges of these plates (13) are tapered in order to facilitate the insertion of the straws. The slot containing the straws is closed at its lower end by the block (14) of plastic material, with a groove (19) in which to receive the lower ends of the straws. Above the slot are the two plates (15,16) of plastic material with the flexible rubber plate (17) between them. Into the latter a slit is cut, through which the straw can be introduced or withdrawn. The cooling elements on both sides consist of the plates (18,18', 5,5', 7,7') with, between them, the two layers of Peltier blocks (4,4', 6,6'). The outermost plates (7,7') are provided with cooling channels (8,8').

Figure 8A:
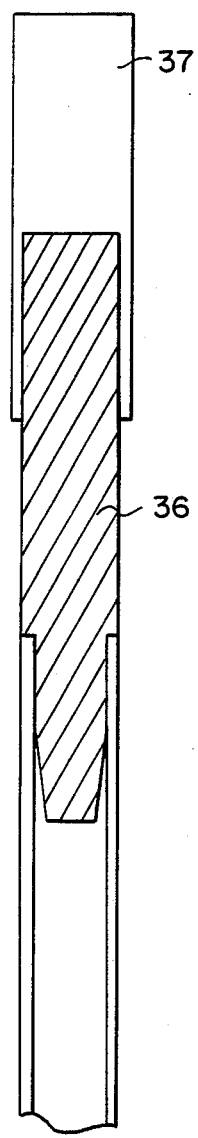
Figure 8B:
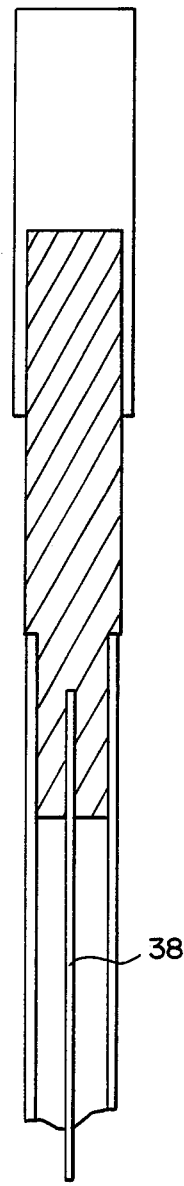
Figure 8C:
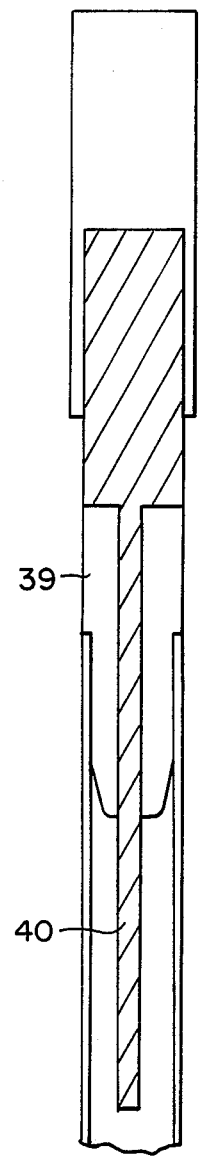

The straws to be used with this type of apparatus have to be long enough, so that, when they are inserted into the slot, their upper end extends beyond the lips of the rubber plate (17) and can be grasped for removal. Another possibility is the use of straws, the upper end of which is closed by a long cylindrical stopper, preferably made of plastic material, whose end protrudes from the slit of the rubber plate (17), as shown in FIG. 2. Straws with such stoppers are shown in FIG. 8a–c.

Figure 3A:
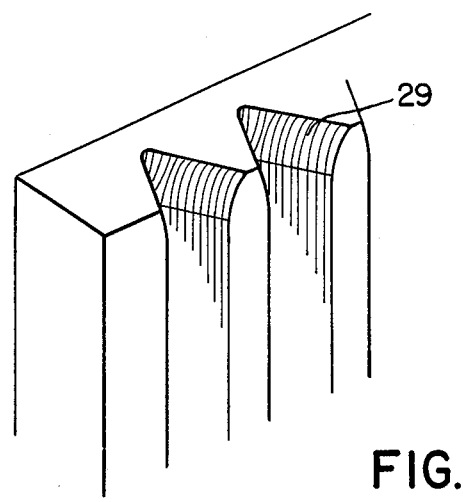
Figure 3B:
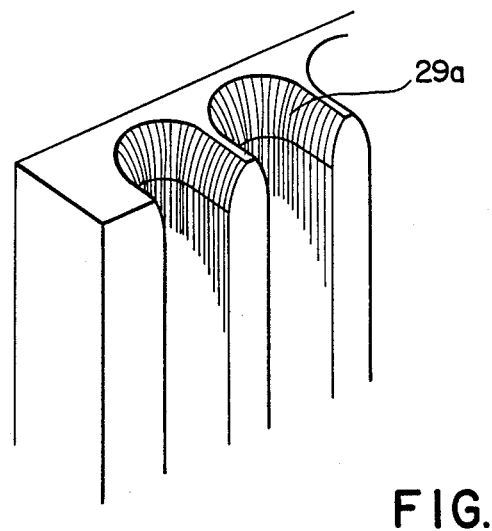

FIG. 3 shows a cooling block, whose outer surfaces are provided with grooves (29, 29a) for receiving straws. (29) and (29a) respectively represent grooves of two different cross sections.

Figure 4:
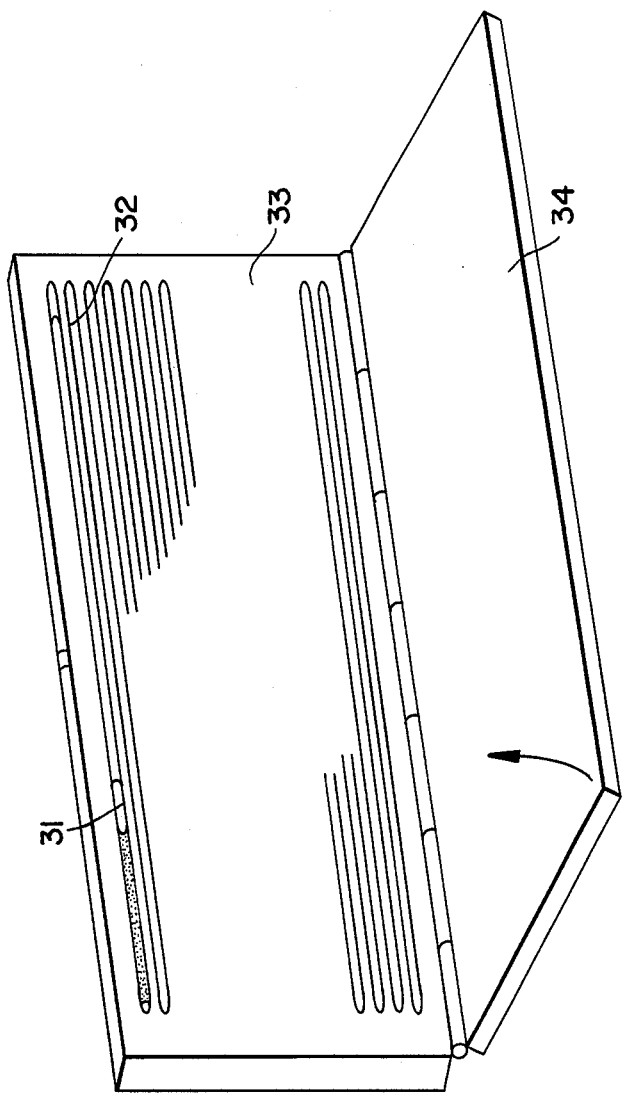

FIG. 4 shows one possible form of a cooling block which can be used as a module or cassette to be inserted into the cooling zone. The module is made of two parts (33, 34) that can be hinged apart to introduce or withdraw the straws (31) containing the biological samples. When the module is closed, the samples are completely enclosed by the walls (32) of the module. When using other vessels instead of straws, the cavities have to be shaped differently, according to the form of the vessels.

Figure 5:
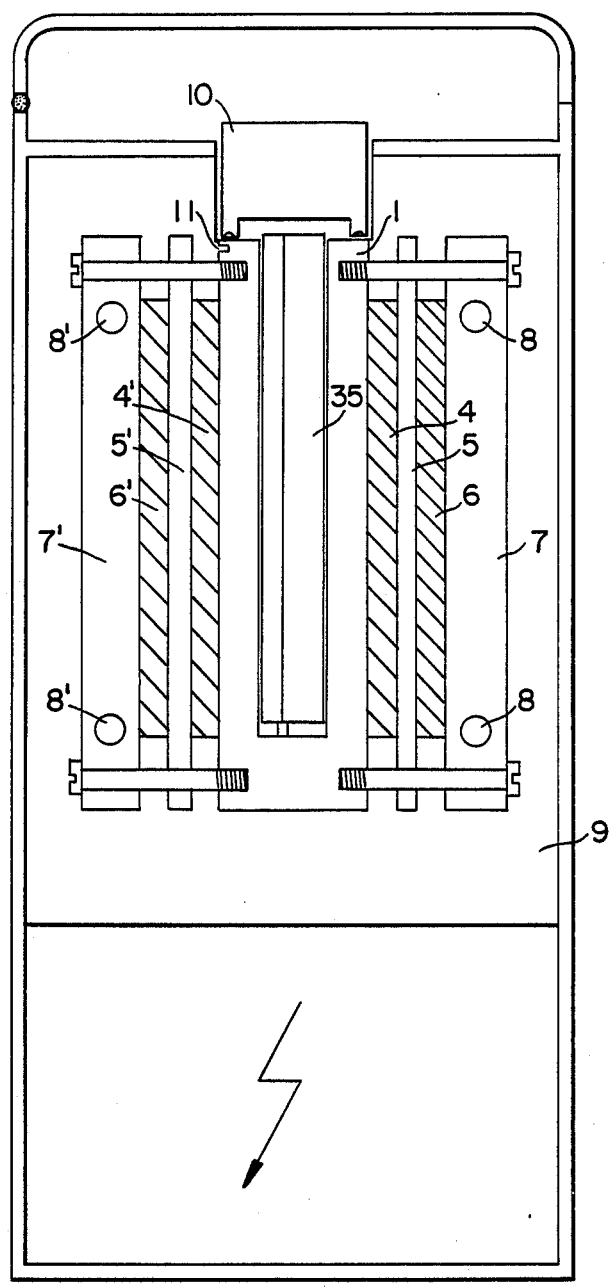

FIG. 5 shows a possible design of the deep freezing apparatus, into which modules (35) containing the vessels with the samples can be introduced. The inside of these modules can be designed in different shapes in order to receive vessels of different form and size. The thermal insulation is represented by the mantle (9) and the lid (10).

Figure 6:
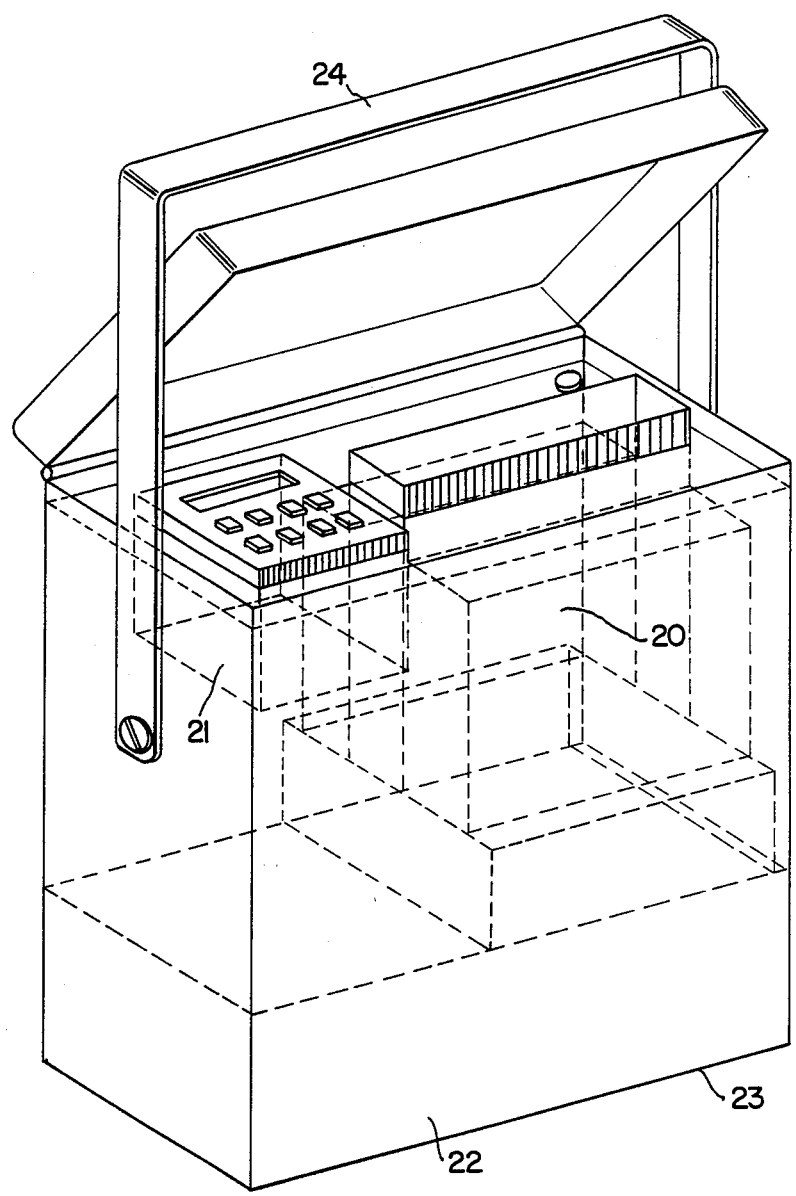

FIG. 6 is a perspectivic view of a combined apparatus, in which the cooling and freezing device (20), the electronic control circuit (21) and the power supply (22) are enclosed in a housing (23) with the the handle (24) for carrying. Instead of the power supply (22), or additionally, the unit can be provided with a battery for use without a mains connection.

Figure 7A:
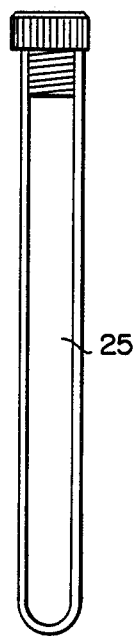
Figure 7B:
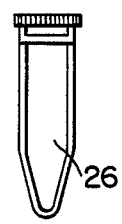
Figure 7C:

In FIG. 7 different forms of the vessels, in which to enclose the biological samples, are displayed: An ampulla (25), a tube (26) and a straw (27).

FIG. 8a–c show different designs of stoppers for closing straws, all of them consisting of a part (36) made of metal and a part (37) made of an insulating plastic material. In FIG. 8b the metallic part is extending in a needle-like shape (38) into the straw, and the tip of this part may dip into the liquid part of the biological sample. In FIG. 8c a design is shown with the needle-like part (40) surrounded by a plastic collar (39) fitting into the straw. In all three designs the metallic part above the end of the straw is made of exactly the diameter of a straw in order to fit closely between the cooling plates.

Figure 9:
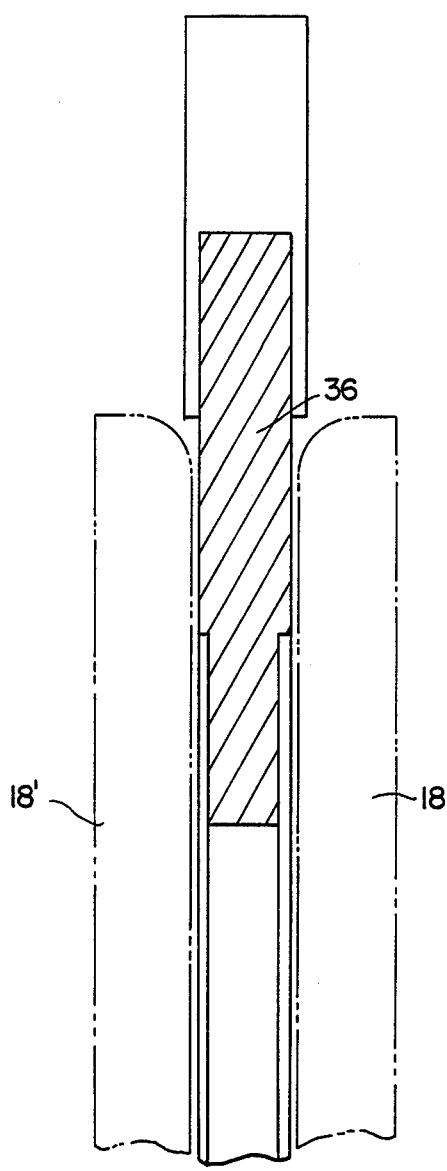

FIG. 9 shows the upper end of a straw with a stopper according to FIG. 8a with the metallic part (36) of the stopper fitting closely between the two cooling plates (18) and (18').

In the following example the construction of one possible form of the apparatus according to the invention is described in more detail, whereby the figures given for the dimensions represent possibilities which are not intended to limit the scope of the invention.

EXAMPLE

Two aluminium plates (18,18') with a thickness of 15 mm, 120 mm long and 80 mm wide, are arranged in parallel at a distance of 1.95 mm (corresponding to the diameter of a straw). The slot is covered at its shorter edges by strips of insulating material of 5 mm thickness. One of the longer edges remains open and the other one is closed by a block of plastic material (14) into which a groove has been milled. On each of the outer sides of the plates (18,18') two blocks of Peltier elements with the dimensions 55×27×4 mm are mounted, while maintaining a good thermal contact between the blocks and the plates. The Peltier blocks are covered by two plates (5,5') of the same dimensions as the plates (18,18'). Onto them a second cooling layer (6,6'), consisting of four Peltier blocks on each side is fixed. This layer is covered by the plates (7.7'), which contain the cooling channels (8,8'). Cooling weater is led through these channels, entering one end of a channel 8 on one side and leaving at the end of one channel (8') on the other side.

The Peltier elements are fed in series by a direct current of 9 A, whereby a voltage drop of 4 V results for each block of Peltier elements. In the cooling slot between the plates (18,18'), into which 50 straws are inserted, a maximum temperature drop of 3.5° C./min can be attained between room temperature and −10° C., and of 0.5° C. between −10° C. and −35° C. Typical optimum values in the freezing of biological specimen are about −0.5° C./min between +20° C. and −7° C. and then, after a stop of several minutes, −0.3° C./min between −7° C. and −35° C. The total time needed to freeze the samples will be about 2½ hours. Thus the electric power available in the apparatus is sufficient to freeze the biological samples along the optimum temperature curve.

We claim:

1. Apparatus for cooling and deep freezing samples of biological material enclosed in vessels, consisting of two parallel plate-like cooling elements which between them confine a cooling zone, characterized in that each of said cooling elements is a layered structure of at least two cooling layers stacked onto one another alternatingly with metal plates of high thermal conductivity, each of said cooling layers consisting of one or more blocks of Peltier elements arranged thermally in parallel, whereby the metal plates, which constitute the outer boundaries of the arrangement, are equipped with means for external cooling.

2. Apparatus according to claim 1 for cooling and deep freezing samples of biological material enclosed in vessels, characterized in that the cooling zone enclosed between the cooling elements consists of a metallic block of high thermal conductivity which is provided with cavities to receive the vessels containing the samples of biological material.

3. Apparatus according to claim 2, characterized in that the metallic cooling block is an interchangeable module which, by simple manipulation, can be inserted into or removed from the freezing apparatus, whereby different modules may comprise different cavity arrangements to receive vessels of different shape.

4. Apparatus according to claim 3, characterized in that the metallic cooling module is composed of two parts easily to be separated or hinged, said two parts enclosing the cavities for receiving the vessels, whereby the cavities are only accessible when the two parts are separated or hinged apart.

5. Apparatus according to claim 2, especially suited for vessels in the form of long, narrow tubes, so-called straws, characterized in that the two surfaces of the metallic cooling block adjoining the cooling elements contain parallel grooves for receiving the straws.

6. Apparatus according to claim 2, characterized in that the metallic block comprises the innermost metallic plates of the two layered cooling elements, said plates being connected at the bottom of the cooling zone and consisting of one single piece of metal.

7. Apparatus according to claim 1, especially suited for vessels in the form of so-called straws, characterized in that the cooling zone is a narrow slot confined at its sides by the innermost parallel metallic plates of the two layered cooling elements, the width of said slot corresponding exactly to the thickness of the straws.

8. Apparatus according to claim 7, characterized in that the cooling slot, on its accessible side, is closed by a flexible rubber plate comprising a slit, whose sides, opposed to one another, form a tight seal, through which the straws containing the samples can be introduced into or withdrawn from the cooling zone, without removing the rubber plate.

9. Apparatus according to claim 8, in which the straws containing the biological samples, are shorter than the depth of the cooling slot and are provided with a cylindrical heat-insulating stopper extending outwards from the slit.

10. Apparatus according to claim 9, wherein the cylindrical insulating stopper is partly made of metal and partly of plastic material, whereby the metallic portion of the stopper is inserted into the straw and extends beyond the end of the straw, this extending part being of exactly the diameter of the straw and being in heat-conducting contact with the innermost plates of the cooling elements, and whereby the outer part of the stopper protruding out of the cooling slot is made of a heat-insulating material.

11. Apparatus according to claim 10, characterized in that the metallic portion of the stopper extends into the straw as a needlelike process of a length that its tip is able to dip into the liquid part of the biological specimen.

12. Apparatus according to claim 1, characterized in that all outer surfaces, which are not provided with external cooling means, are covered with a thermal insulating layer, whereby at the entrance to the cooling zone, said insulating layer is formed by a removable cover.

13. Apparatus according to claim 1, characterized in that the metal of high thermal conductivity is aluminium.

14. Apparatus according to claim 1, characterized in that the the device for externally cooling the outermost plates of the cooling elements consists of channels inside said plates, through which a fluid or gaseous cooling medium is circulated.

15. Apparatus according to claim 1, characterized in that the device for externally cooling the outermost plates of the two cooling elements comprises cooling ribs on the outer surface of said plates, against which air or another gas can be blown.

16. Apparatus according to claim 1, characterized in that, during the cooling and freezing procedure, the temperature in the cooling zone is controlled by an automatic system consisting of one or more temperature sensors in the cooling zone and/or in the adjoining metal plates and of an electronic device, which, guided by the temperature sensors, controls the energy output of the cooling elements according to a predetermined program for the temperature of the cooling zone, whereby this device may comprise an instrument for indicating and/or recording the temperature inside the cooling zone.

17. Apparatus according to claim 16, characterized in that the control apparatus is directed by a programmable microprocessor, through which the Peltier elements are fed by a pulsed d.c. source, whereby the input to the alimentation unit is a chopped a.c., and whereby the temperature programme comprises at least one slope function, which causes a constant temperature change in the cooling zone during a predetermined time or temperature interval.

18. Apparatus according to claim 1, characterized in that the cooling and freezing device, the electronic control system and the d.c. power supply are enclosed together in a portable housing box.

19. The use of the apparatus according to claim 1, for deep freezing samples of biological material contained in vessels.

20. The use of the apparatus according to claim 1, for cooling samples of biological material contained in vessels to temperatures above the their freezing point and maintaining them at these temperatures.

* * * * *